(12) United States Patent
Alanine et al.

(10) Patent No.: US 6,432,985 B2
(45) Date of Patent: Aug. 13, 2002

(54) NEUROPROTECTIVE SUBSTITUTED PIPERIDINE COMPOUNDS WITH ACTIVITY AS NMDA NR2B SUBTYPE SELECTIVE ANTAGONISTS

(75) Inventors: Alexander Alanine, Schlierbach (FR); Bernd Buettelmann, Schopfheim (DE); Marie-Paule Heitz Neidhart, Hagenthal le Bas (FR); Georg Jaeschke, Basel (CH); Emmanuel Pinard, Linsdorf (FR); Rene Wyler, Zurich (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/811,888

(22) Filed: Mar. 19, 2001

(30) Foreign Application Priority Data

Apr. 25, 2000 (EP) .............................. 00108769

(51) Int. Cl.⁷ .................. A61K 31/445; C07D 211/40; C07D 211/44
(52) U.S. Cl. .................. 514/328; 546/217; 546/219
(58) Field of Search ................ 546/217, 219; 514/328

(56) References Cited

FOREIGN PATENT DOCUMENTS

| EP | 824 098 | 2/1998 |
|---|---|---|
| WO | WO 97/23216 | 7/1997 |
| WO | WO 97/23458 | 7/1997 |

*Primary Examiner*—Alan L. Rotman
(74) *Attorney, Agent, or Firm*—George W. Johnston; Patricia S. Rocha-Tramaloni; Arthur D. Dawson

(57) ABSTRACT

The invention relates to a compound of the formula

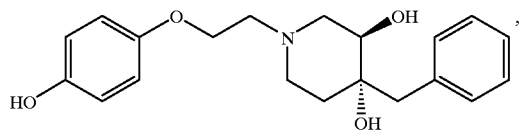

its R,R-, S,S-enantiomers and racemic mixtures thereof and to their pharmaceutically acceptable acid addition salts.

The compound of formula I and its R,R- and S,S-enantiomers may be used as medicaments for the treatment of diseases, wherein the therapeutic indications include acute forms of neurodegeneration caused by stroke or brain trauma; chronic forms of neurodegeneration such as Alzheimer's disease, Parkinson's disease, Huntington's disease or ALS (amyotrophic lateral sclerosis); neurodegeneration associated with bacterial or viral infections, and, diseases such as schizophrenia, anxiety, depression and chronic/acute pain.

11 Claims, No Drawings

NEUROPROTECTIVE SUBSTITUTED PIPERIDINE COMPOUNDS WITH ACTIVITY AS NMDA NR2B SUBTYPE SELECTIVE ANTAGONISTS

FIELD OF INVENTION

The present invention is generally related to substituted piperidine compounds and more particularly to compounds with activity as NMDA receptor subtype selective blockers that have low activity as blockers of hERG potassium channels.

The present invention relates to the compound of formula

I

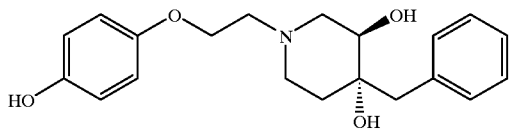

to its R,R- and S,S-enantiomers and to their pharmaceutically acceptable acid addition salts.

The compounds of the present invention are NMDA (N-methyl-D-aspartate)-receptor-subtype selective blockers, which have a key function in modulating neuronal activity and plasticity which makes them key players in mediating processes underlying development of CNS including learning and memory formation and function.

Under pathological conditions of acute and chronic forms of neurodegeneration overactivation of NMDA receptors is a key event for triggering neuronal cell death. NMDA receptors are composed of members from two subunit families, namely NR-1 (8 different splice variants) and NR-2 (A to D) originating from different genes. Members from the two sub-unit families show a distinct distribution in different brain areas. Heteromeric combinations of NR-1 members with different NR-2 sub-units result in NMDA receptors, displaying different pharmacological properties. Possible therapeutic indications for NMDA receptor subtype specific blockers include acute forms of neurodegeneration caused, e.g., by stroke or brain trauma; chronic forms of neurodegeneration such as Alzheimer's disease, Parkinson's disease, Huntington's disease or ALS (amyotrophic lateral sclerosis); neurodegeneration associated with bacterial or viral infections, diseases such as schizophrenia, anxiety and depression and acute/chronic pain.

Objects of the present invention are novel compounds of formula I, its R,R- and S,S-enantiomers, racemic mixtures of these enantiomers and pharmaceutically acceptable salts of these novel compounds; their use in the treatment or prophylaxis of diseases caused by overactivation of respective NMDA receptor subtypes, which include acute forms of neurodegeneration caused, e.g., by stroke or brain trauma; chronic forms of neurodegeneration such as Alzheimer's disease, Parkinson's disease, Huntington's disease or ALS (amyotrophic lateral sclerosis); neurodegeneration associated with bacterial or viral infections, and diseases such as schizophrenia, anxiety, depression and acute/chronic pain; the use of these compounds for manufacture of corresponding medicaments; processes for the manufacture of these novel compounds; and medicaments containing the compounds of the invention.

The term "pharmaceutically acceptable acid addition salts" embraces salts with inorganic and organic acids, such as hydrochloric acid, nitric acid, sulfuric acid, lactic acid, phosphoric acid, citric acid, formic acid, fumaric acid, maleic acid, acetic acid, succinic acid, tartaric acid, methane-sulfonic acid, p-toluenesulfonic acid and the like.

4-Hydroxy-piperidin derivatives are described, for example in EP 824 098, in which the piperidine ring is substituted by one hydroxy group in 4-position. These compounds are described to possess activities on the NMDA receptor and are useful in the treatment of acute forms of neurodegeneration caused, for example, by stroke and brain trauma, and chronic forms of neurodegeneration such as Alzheimer's disease, Parkinson's disease, ALS (amyotrophic lateral sclerosis), neurodegeneration associated with bacterial or viral infections and acute/chronic pain.

It is known from EP 824 098 that these compounds are good NMDA receptor subtype specific blockers with a high affinity for NR2B subunit containing receptors and low affinity for NR2A subunit containing receptors.

Activity versus $\alpha_1$-adrenergic receptors is also low and the compounds are active in vivo against audiogenic seizures in mice in the low mg/kg range. Importantly, these compounds were neuroprotective in an animal stroke model, namely, a permanent occlusion of the middle cerebral artery. However, in vitro and in vivo cardiotoxicity studies showed that these compounds had the propensity to prolong cardiac action potential duration in vitro and consequently the 'QT'-interval in vivo and thus, had a potential liability to produce cardiac arrhythmias. The ability of such compounds to prolong the cardiac action potential was identified as being due to an action at the hERG type potassium channel, which is important for action potential repolarisation in humans and other species, and most compounds known to prolong the QT-interval in man are active at blocking this channel. Thus, the compounds of the prior art block heterologously recombinant human ERG potassium channels.

It has now surprisingly been found that the following preferred compounds of formula I (3R,4R) and (3S,4S)-4-benzyl-1-[2-(4-hydroxy-phenoxy)-ethyl]-piperidine-3,4-diol, (3R,4R)-4-benzyl-1-[2-(4-hydroxy-phenoxy)-ethyl]-piperidine-3,4-diol and (3S,4S)-4-benzyl-1-[2-(4-hydroxy-phenoxy)-ethyl]-piperidine-3,4-diolare NMDA NR2B subtype selective antagonists. These preferred compounds of the invention share the highly specific subtype selective blocking properties of compounds of the prior art, for example of 1-[2-(4-hydroxy-phenoxy)-ethyl]-4-(4-methyl-benzyl)-piperidin-4-ol (EP 824 098), and are neuroprotectants in vivo, unlike the compounds of EP 824098, the preferred compounds of the invention are significantly less active as blockers of the hERG potassium channels and, thus, are much less likely to have pro-arrhythmic activity in man.

In the following table the high selectivity of compounds of the present invention is demonstrated.

| Selectivity profile of NMDA NR2B subtype selective antagonists | | | |
|---|---|---|---|
| Compound | Inhibition of [3H]-Ro 25-6981 binding IC$_{50}$ ($\mu$M)$^a$ | Inhibition of [3H]-Prazosin binding IC$_{50}$ ($\mu$M)$^b$ | Inhibition of hERG K+ current IC$_{50}$ ($\mu$M) (effect (%) at 10 $\mu$M$^c$) |
| EP 824098 1-[2-(4-hydroxy-phenoxy)-ethyl]-4-(4-methyl-benzyl)-piperidin-4-ol | 0.010 | 3.5 | 0.69 $\mu$M |
| I (racemate) | 0.045 | 27 | >10 $\mu$M (45%), |

-continued

Selectivity profile of NMDA NR2B subtype selective antagonists

| Compound | Inhibition of [3H]-Ro 25-6981 binding IC$_{50}$ ($\mu$M)[a] | Inhibition of [3H]-Prazosin binding IC$_{50}$ ($\mu$M)[b] | Inhibition of hERG K+ current IC$_{50}$ ($\mu$M) (effect (%) at 10 $\mu$M[c]) |
|---|---|---|---|
| I-1 (R,R) | 0.038 | 25 | >10 $\mu$M (44%) |
| I-2 (S,S) | 0.039 | 30 | >10 $\mu$M (40%) |

[a]Inhibition of [3H]-Ro-6981 binding indicates affinity for NMDA NR2B subunit containing receptors.
[b]Inhibition of [3H]-Prazosin binding indicates affinity for $\alpha_1$-adrenergic receptors.
[c]Indicates potency for blockade of recombinant human ERG potassium channels expressed in a mammalian cell line (chinese hamster ovary cells, CHO).

The novel compounds of formula I and their pharmaceutically acceptable salts can be prepared by methods known in the art, for example by a process described below, which process comprises reacting a compound of formula

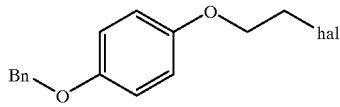

with a compound of formula

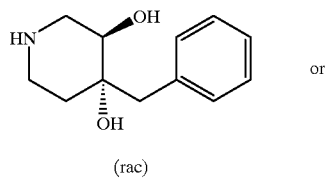
(rac)

VII

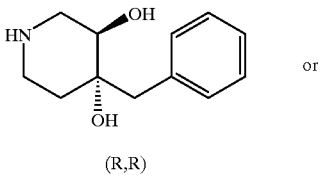
(R,R)

or

XI

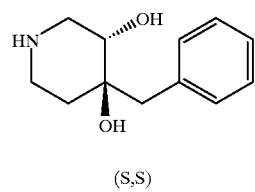
(S,S)

XV and deprotecting the hydroxy group to give compounds of formulae

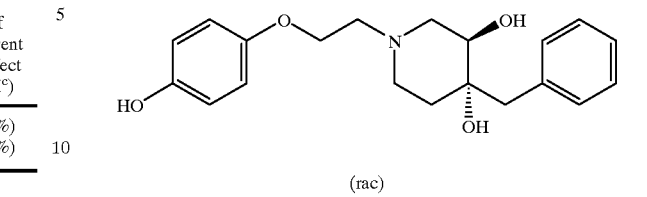
(rac)

I

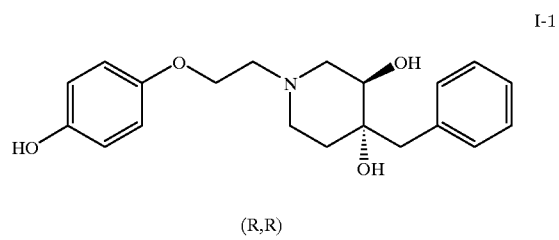
(R,R)

I-1

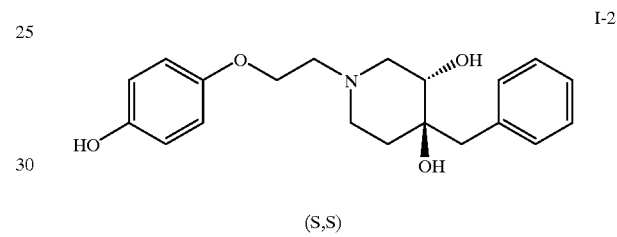
(S,S)

I-2 and, preferably, converting the compounds obtained into a pharmaceutically acceptable acid addition salts.

In accordance with the described process variant, 4-benzyl-3,4-dihydroxy-piperidine, (3R,4R)-4-benzyl-3,4-dihydroxy-piperidine or (3S,4S)-4-benzyl-3,4-dihydroxy-piperidine is treated with 1-benzyloxy-4-(2-chloro-ethoxy)-benzene in the presence of K$_2$CO$_3$. The reaction is carried out at about 80–100° C. The O-protecting group is then cleaved off in conventional manner, for example by hydrogenating in the presence of Pd/C.

The acid addition salts of the compounds of formula I are especially well suited for a pharmaceutical use.

The following schemes 1 and 2 describe the preparation of the compound of formula I and its desired enantiomeric forms. The starting materials of formulae III and 1-benzyloxy-4-(2-chloro-ethoxy)-benzene are known compounds or can be prepared by methods known in the art.

In schemes 1 and 2 the following abbreviations have been used:

| | |
|---|---|
| Z—Cl | benzylchloroformate |
| MCPBA | meta-chloroperbenzoic acid |
| DMAP | dimethylaminopyridine |
| Pd/C | palladium on carbon catalyst |
| DMF | dimethylformamide |
| Bn | benzyl |

US 6,432,985 B2
Scheme 1
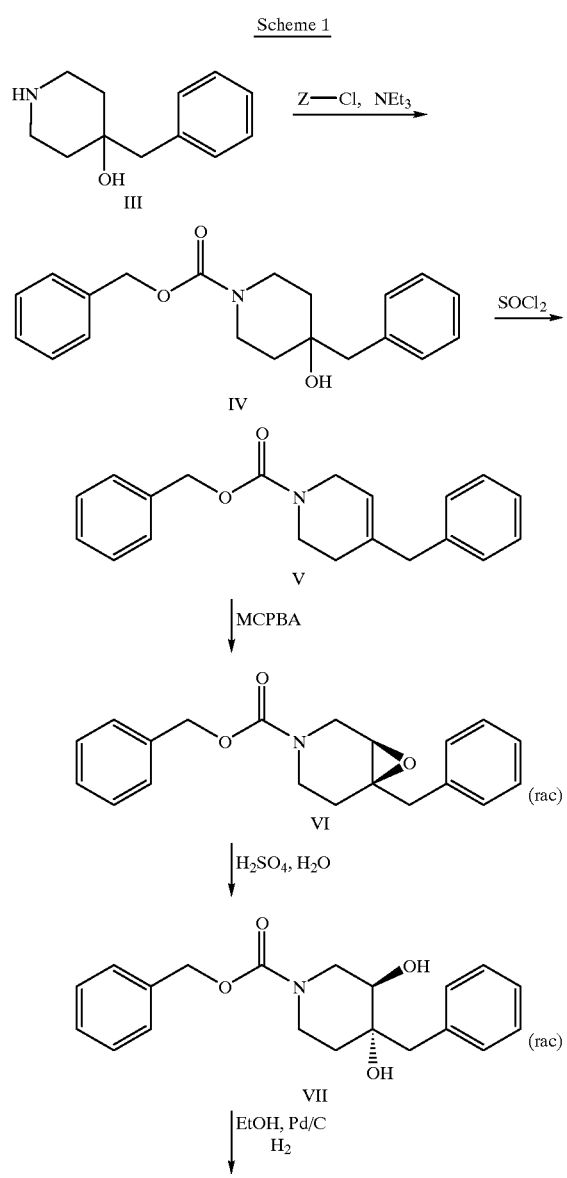
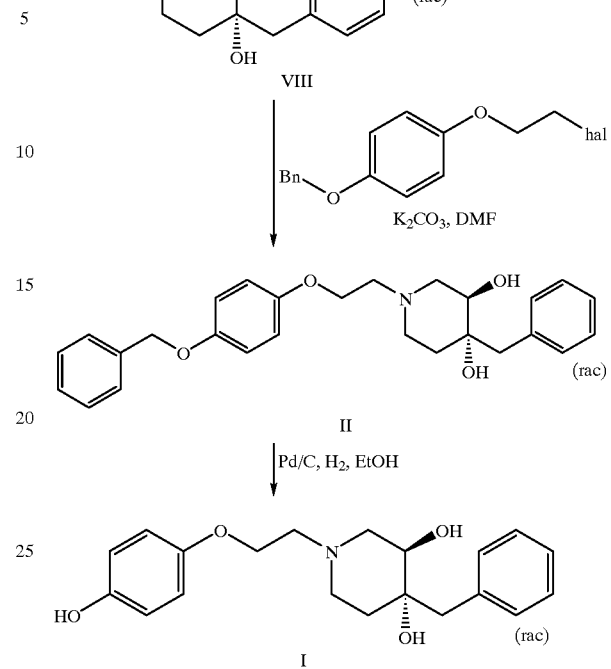
wherein "hal" may be chloro or bromo.
Scheme 2

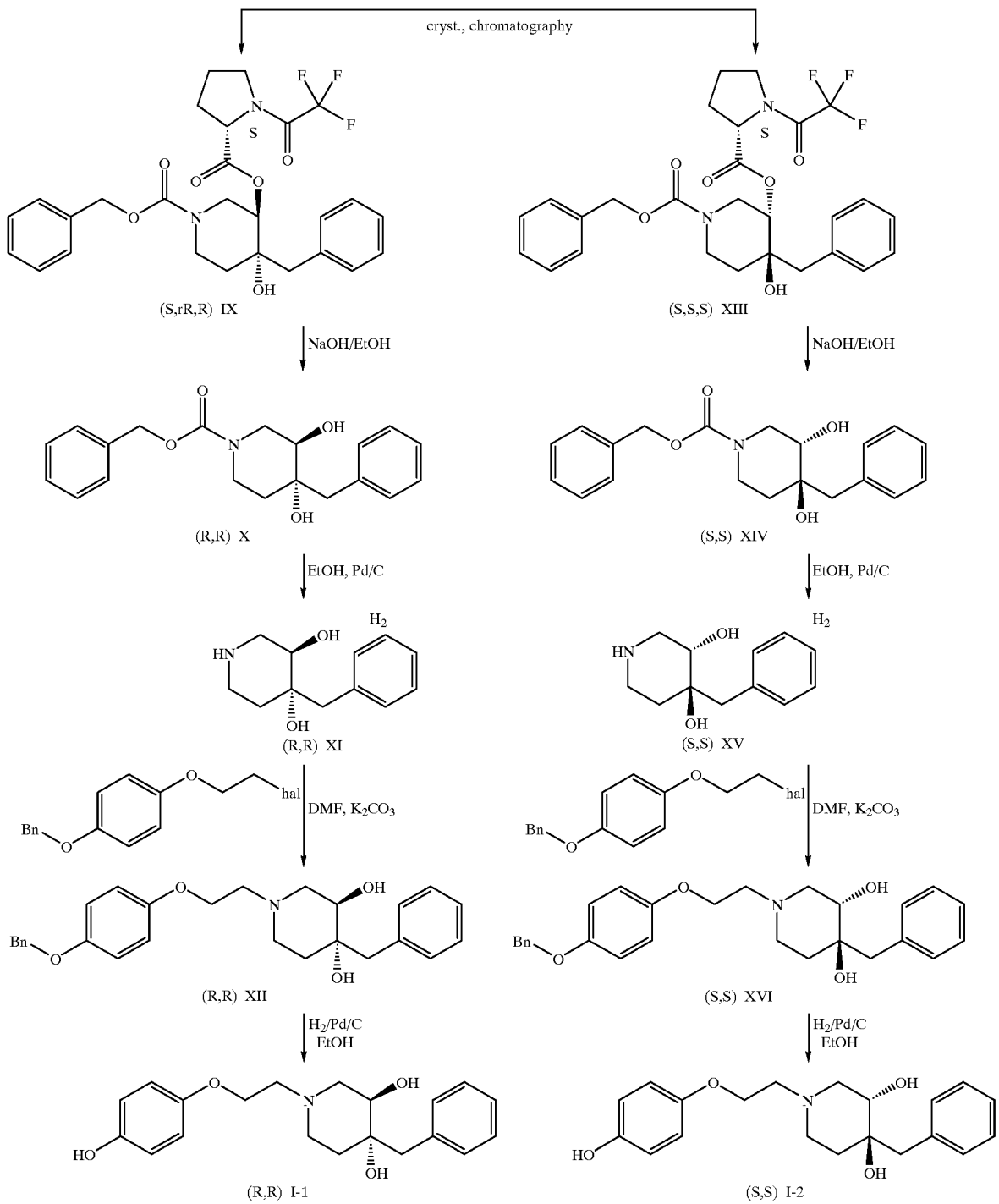

The detailed description of the above mentioned processes is described in Examples 1–17.

As mentioned earlier, the compounds of formula I and their pharmaceutically acceptable addition salts possess valuable pharmacodynamic properties. They are NMDA-receptor subtype selective blockers, which have a key function in modulating neuronal activity and plasticity which makes them key players in mediating processes underlying development of CNS as well as learning and memory formation.

The compounds were investigated in accordance with the test given hereinafter.

Method 1

3H-Ro 25-6981 Binding(Ro 25-6981 is [R-(R*, S*)]-α-(4-Hydroxy-phenyl)-β-methyl-4-(phenyl-methyl)-1-piperidine propanol)

Male Füllinsdorf albino rats weighing between 150–200 g were used. Membranes were prepared by homogenization of the whole brain minus cerebellum and medulla oblongata with a Polytron (10,000 rpm, 30 seconds), in 25 volumes of a cold Tris-HCl 50 mM, EDTA 10 mM, pH 7.1 buffer. The homogenate was centrifuged at 48.000 g for 10 minutes at 4° C. The pellet was resuspended using the Polytron in the same volume of buffer and the homogenate was incubated at 37° C. for 10 minutes. After centrifugation the pellet was homogenized in the same buffer and frozen at −80° C. for at least 16 hours but not more than 10 days. For the binding assay the homogenate was thawed at 37° C., centrifuged and the pellet was washed three times as above in a Tris-HCl 5 mM, pH 7.4 cold buffer. The final pellet was resuspended in the same buffer and used at a final concentration of 200 μg of protein/ml.

[3H]-Ro 25-6981 binding experiments were performed using a Tris-HCl 50 mM, pH 7.4 buffer. For displacement experiments 5 nM of 3H-Ro 25-6981 were used and non specific binding was measured using 10 μM of tetrahydroisoquinoline and usually it accounts for 10% of the total. The incubation time was 2 hours at 4° C. and the assay was stopped by filtration on Whatman GF/B glass fiber filters (Unifilter-96, Packard, Zürich, Switzerland). The filters were washed 5 times with cold buffer. The radioactivity on the filter was counted on a Packard Top-count microplate scintillation counter after addition of 40 mL of microscint 40 (Canberra Packard S.A., Zürich, Switzerland).

The effects of compounds were measured using a minimum of 8 concentrations and repeated at least once. The pooled normalized values were analyzed using a non-linear regression calculation program which provide $IC_{50}$ with their relative upper and lower 95% confidence limits (RS1, BBN, USA).

Method 2

3H-Prazosin Binding

Male Füllinsdorf albino rats weighing between 150–200 g were used. Membranes were prepared by homogenization of the whole brain minus cerebellum and medulla oblongata with a Plytron (10,000 rpm, 30 seconds), in 25 volumes of a cold Tris-HCl 50 mM, EDTA 10 mM, pH 7.1 buffer. The homogenate was centrifuged at 48.000 g for 10 minutes at 4° C. The pellet was resuspended using the Polytron in the same volume of buffer and the homogenate was incubated at 37° C. for 10 minutes. After centrifugation the pellet was homogenized in the same buffer and frozen at −80° C. for at least 16 hours but not more than 10 days. For the binding assay the homogenate was thawed at 37° C., centrifuged and the pellet was washed three times as above in a Tris-HCl 5 mM, pH 7.4 cold buffer. The final pellet was resuspended in the same buffer and used at a final concentration of 200 mg of protein/ml.

3H-Prazosin binding experiments were performed using a Tris-HCl 50 mM, pH 7.4 buffer. For displacement experiments 0.2 nM of 3H-Prazosine were used and non specific binding was measured using 100 mM of Chlorpromazine. The incubation time was 30 minutes at room temperature and the assay was stopped by filtration on Whatman GF/B glass fiber filters (Unifilter-96, Canberra Packard S.A., Zürich, Switzerland). The filters were washed 5 times with cold buffer. The radioactivity on the filter was counted on a Packard Top-count microplate scintillation counter after addition of 40 ml of microscint 40 (Canberra Packard S.A., Zürich, Switzerland). The effects of compounds were measured using a minimum of 8 concentrations and repeated at least once. The pooled normalized values were analyzed using a non-linear regression calculation program which provide $IC_{50}$ with their relative upper and lower 95% confidence limits (RS1, BBN, USA).

The thus-determined activity of compounds in accordance with the invention is in the range of 0.039–0.045 (in μM), as described in the table above.

Method 3

Methods for Studying the Inhibition of the hERG $K^+$ Channel

CHO cells were stably transfected by a pcDNA3-hERG expression vector containing a SV40-neo cassette for selection. Cells were thinly plated into 35 mm dishes and used for the electrophysiological experiment ½-3 d later.

During the experiment the cells were continuously superfused with an extracellular saline containing (in mM): NaCl 150, KCl 10, $MgCl_2$ 1, $CaCl_2$ 3, HEPES 10 (pH=7.3 by addition of NaOH). A 10-mM stock solution of the test compound was made from pure DMSO. Test solution were made by at least 1000-fold dilution of the stock solution into the extracellular saline. The glass micropipettes for whole-cell patch-clamp recording were filled with a containing (in mM): KCl 110, BAPTA 10, HEPES 10, $MgCl_2$ 4.5, $Na_2ATP$ 4, $Na_2$-phosphocreatine 20, creatine kinase 200 μg/ml (pH= 7.3 by addition of KOH).

The whole-cell configuration of the patch-clamp technique was used for the experiments. Cells were clamped to −80 mV holding potential and repetitively (0.1 Hz) stimulated by a voltage pulse pattern consisting of a 1-s conditioning depolarisation to 20 mV immediately followed by a hyperpolarisation of 50 ms duration to −120 mV. The membrane current was recorded for at least 3 min (18 stimuli) before compound application (control), and then for another two 3-min intervals in presence of two different concentrations of the compound. The current amplitudes ($I_{test}$) at the end of each compound application interval were divided by the mean current amplitude ($I_{control}$) during the initial control period to calculate the percentage effect of the compound:

$$\text{effect } (\%) = (1 - I_{test}/I_{control}) \cdot 100.$$

Compound concentrations were chosen in decade steps (usually 1 and 10 μM) around the expected 50% inhibitory concentration ($IC_{50}$). If after the first experiment the $IC_{50}$ turned out to lie outside the range between the two chosen concentrations the concentrations were changed to bracket the $IC_{50}$ in the following experiments. The compound was tested on at least three cells. Its $IC_{50}$ was then estimated from the population of all percent-effect values by non-linear regression using the function effect=$100/(1-IC_{50}/\text{concentration})^{Hill}$). Concentrations higher than 10 μM were not tested. If 10 μM of the compound turned out to produce less than 50% effect, IC50 was labelled as ">10 μM" and the compound was characterised by the average effect seen at 10 μM.

The compounds of formula I and their salts, as herein described, together with pharmaceutically inert excipients are preferably incorporated into standard pharmaceutical dosage forms, for example, for oral or parenteral application with the usual pharmaceutical adjuvant materials, for example, organic or inorganic inert carrier materials, such as, water, gelatin, lactose, starch, magnesium stearate, talc, vegetable oils, gums, polyalkylene-glycols and the like. Examples of pharmaceutical preparations in solid form are tablets, suppositories, capsules, or in liquid form are solutions, suspensions or emulsions. Pharmaceutical adjuvant materials include preservatives, stabilizers, wetting or emulsifying agents, salts to change the osmotic pressure or to act as buffers. The pharmaceutical preparations can also contain other therapeutically active substances.

The daily dose of compounds of formula I to be administered varies with the particular compound employed, the chosen route of administration and the recipient. Representative of a method for administering the compounds of formula I is by the oral and parenteral type administration route. An oral formulation of a compound of formula I is preferably administered to an adult at a dose in the range of 1 mg to 1000 mg per day. A parenteral formulation of a compound of formula I is preferably administered to an adult at a dose in the range of from 5 to 500 mg per day.

The invention is further illustrated in the following examples.

EXAMPLE 1

4-Benzyl-4-Hydroxy-Piperidine-1-carboxylic Acid Benzyl Ester

To a solution of 5.0 g (26.2 mmol) of 4-hydroxybenzylpiperidine in 50 ml $CH_2Cl_2$ were added under argon 5.5 ml (39.3 mmol) of $Et_3N$ and 3.7 ml (26.2 mmol) of benzylchloroformate at 0° C. After stirring the reaction mixture for 3 hours at r.t. 100 ml 1N HCl were added and the aqueous phase was extracted twice with $CH_2Cl_2$ and the combined organic layers were washed with 50 ml water, dried over $MgSO_4$ and the solvent was removed under reduced pressure to give the crude product. Purification by chromatography over silica gel (hexane/ethyl acetate 4:1 to 2:1) yielded 3.9 g 4-benzyl-4-hydroxy-piperidine-1-carboxylic acid benzyl ester (11.9 mmol, 48%) as a yellow oil.

MS: m/e=326(M+1)

EXAMPLE 2

4-Benzyl-3,6-Dihydro-2H-Pyridine-1-Carboxylic Acid Benzyl Ester

To a solution of 40.0 g (123 mmol) of 4-benzyl-4-hydroxy-piperidine-1-carboxylic acid benzyl ester in 250 ml $CH_2Cl_2$ were added 39.6 ml (492 mmol) pyridine and at 0° C. 17.8 ml (246 mmol) of $SOCl_2$. The reaction mixture was stirred for 30 min. at 0° C. and then 250 ml of aqueous (2N) HCl were added. The aqueous phase was extracted twice with $CH_2Cl_2$ and the combined organic layers were washed with water, dried over $MgSO_4$ and the solvent was removed under reduced pressure to give 36.3 g (118 mmol, 96%) of 4-benzyl-3,6-dihydro-2H-pyridine-1-carboxylic acid benzyl ester as an orange oil.

MS: m/e=308(M+1)

EXAMPLE 3

(1R,6S) and (1S,6R)-6-Benzyl-7-Oxa-3-Aza-Bicyclo[4.1.0]Heptane-3-Carboxylic Acid Benzyl Ester To a solution of 36.0 g (117 mmol) of 4-benzyl-3,6-dihydro-2H-pyridine-1-carboxylic acid benzyl ester in 250 ml $CH_2Cl_2$ were added 40.9 g (166 mmol, ~70%) MCPBA. The reaction mixture was stirred for 2 hours and a 1N NaOH-solution was added. The aqueous phase was extracted twice with $CH_2Cl_2$ and the combined organic layers were washed with 1 N NaOH, dried over $MgSO_4$ and the solvent was removed under reduced pressure to give 37.6 g (116 mmol, 99%) of (1R,6S) and (1S,6R)-6-benzyl-7-oxa-3-aza-bicyclo[4.1.0]heptane-3-carboxylic acid benzyl ester as an oil.

MS: m/e=324(M+1)

EXAMPLE 4

(3R,4R) and (3S,4S)-4-Benzyl-3,4-Dihydroxy-piperidine-1-Carboxylic Acid Benzyl Ester To a solution of 37.6 g (116 mmol) of (1R,6S) and (1S,6R)-6-benzyl-7-oxa-3-aza-bicyclo[4.1.0]heptane-3-carboxylic acid benzyl ester in 170 ml THF were added 37 ml $H_2SO_4$ (10%). The reaction mixture was stirred for 16 hours and then concentrated under reduced pressure. The residue was dissolved in ethyl acetate and extracted with sat. $NaHCO_3$. The aqueous phase was extracted twice with ethyl acetate and the combined organic layers were washed with sat. $NaHCO_3$, dried over $MgSO_4$ and the solvent was removed under reduced pressure to give 40.8 g (100%, purity ~95%) of crude (3R,4R) and (3S,4S)-4-benzyl-3,4-dihydroxy-piperidine-1-carboxylic acid benzyl ester.

MS: m/e=342(M+1)

EXAMPLE 5

(4R, 4R), 4-Benzyl-4-Hydroxy-3-((2S)-Trifluoroacetyl-Cyclopentanecarbonyloxy)-Piperidine-1-Carboxylic Acid Benzyl Ester To a solution of 43.0 g (126 mmol) (3R,4R) and (3S,4S)-4-benzyl-3,4-dihydroxy-piperidine-1-carboxylic acid benzyl ester and 23.1 g (189 mmol) DMAP in 600 ml $CH_2Cl_2$ were added dropwise under argon 500 ml (340 mmol, 0.70 N) (S)-N-trifluoroacetyl-prolinechloride. The reaction mixture was stirred for 16 hours at r.t. and then sat. $NaHCO_3$ solution was added. The aqueous phase was extracted three times with $CH_2Cl_2$ and the combined organic layers were washed with sat. $NaHCO_3$ and 1N HCl, dried over $MgSO_4$ and the solvent was removed under reduced pressure to give the crude product. Purification by chromatography on silica gel (hexane:ethyl acetate 4:1 to 1:1) and crystallization from diethylether yielded 17.9 g (33 mmol, 27%) (3R,4R), 4-benzyl-4-hydroxy-3-(2S)-trifluoroacetyl-cyclopentanecarbonyloxy)-piperidine- 1-carboxylic acid benzyl ester.

MS: m/e=535(M+1), (c=1.11, $CH_2Cl_2$).

EXAMPLE 6

(3S,4S), 4-Benzyl-4-Hydroxy-3-((2S)-Trifluoroacetyl-Cyclopentanecarbonyloxy)-Piperidine-1-Carboxylic Acid Benzyl Ester To a solution of 43.0 g (126 mmol) (3R,4R) and (3S,4S)-4-benzyl-3,4-dihydroxy-piperidine-1-carboxylic acid benzyl ester and 23.1 g (189 mmol) DMAP in 600 ml $CH_2Cl_2$ were added under argon 500 ml (340 mmol, 0.70 N) (S)-N-trifluoroacetyl-prolinechloride dropwise. The reaction mixture was stirred for 16 hours at r.t. and then sat. $NaHCO_3$ solution was added. The aqueous phase was extracted three times with $CH_2Cl_2$ and the combined organic layers were washed with sat. $NaHCO_3$ and 1N HCl, dried over $MgSO_4$ and the solvent was removed under reduced pressure to give the crude product. Purification by chromatography on silica gel (hexane:ethyl acetate 4:1 to 1:1) and crystallization from diethylether yielded 14.3 g (27 mmol, 21%) (3S,4S)-4-benzyl-4-hydroxy-3-((2S)-trifluoroacetyl-cyclopentanecarbonyloxy)-piperidine-1-carboxylic acid benzyl ester.

MS: m/e=535(M+1), (c=1.11, $CH_2Cl_2$).

EXAMPLE 7

(3R,4R)-4-Benzyl-3,4-Dihydroxy-Piperidine-1-Carboxylic Acid Benzyl Ester

To a solution of 17.9 g (33.5 mmol) (3R), (4R), 4-benzyl-4-hydroxy-3-((2S)-trifluoroacetyl-cyclopentanecarbonyloxy)-piperidine-1-carboxylic acid benzyl ester in 500 ml EtOH were added 250 ml (250 mmol) of 1 N NaOH. The reaction mixture was stirred for 16 hours and water was then added. The aqueous phase was extracted three times with $CH_2Cl_2$ and the combined organic layers were washed with water, dried over $MgSO_4$ and the solvent was removed under reduced pressure to give 11.2 g (32.8 mmol, 98%) (3R, 4R)-4-benzyl-3,4-dihydroxy-piperidine-1-carboxylic acid benzyl ester as an oil.

MS: m/e=342.3(M+1), $[\alpha]_D^{20}$=−36.75(c=1.02, $CH_2Cl_2$).

EXAMPLE 8

(3S,4S)-4-Benzyl-3,4-Dihydroxy-Piperidine-1-Carboxylic Acid Benzyl Ester

To a solution of 14.3 g (27 mmol) (3S,4S)-4-benzyl-4-hydroxy-3-((2S)-trifluoroacetyl-cyclopentanecarbonyloxy)-piperidine-1-carboxylic acid benzyl ester in 500 ml EtOH were added 250 ml (250 mmol) 1 N NaOH. The reaction mixture was stirred for 16 hours and water was added. The aqueous phase was extracted three times with $CH_2Cl_2$ and the combined organic layers were washed with water, dried over $MgSO_4$ and the solvent was removed under reduced pressure to give 8.4 g (25 mmol, 92%) (3S,4S)-4-benzyl-3,4-dihydroxy-piperidine-1-carboxylic acid benzyl ester as an oil.

MS: m/e=342.3(M+1), $[\alpha]_D^{20}$=35.30(c=1.02, $CH_2Cl_2$).

EXAMPLE 9

(3R,4R) and (3S,4S)-4-Benzyl-3,4-Dihydroxy-Piperidine (3R,4R) and (3S,4S)-4-Benzyl-3,4-dihydroxy-piperidine-1-carboxylic acid benzyl ester 1.46 g (4.3 mmol) was dissolved in 30 ml EtOH and hydrogenated in the presence of 400 mg Pd/C (10%) under atmospheric pressure of $H_2$ at r.t. After 16 hours the reaction was complete and the catalyst was filtered off and the solvent was removed under reduced pressure to give 796 mg (3.8 mmol, 89%) (3R,4R) and (3S,4S)-4-benzyl-3,4-dihydroxy-piperidine as an oil.

MS: m/e=207.1(M).

EXAMPLE 10

(3R,4R)-4-Benzyl-3,4-Dihydroxy-Piperidine (3R,4R)-4-benzyl-3,4-dihydroxy-piperidine-1-carboxylic acid benzyl ester 11.0 g (32 mmol) was dissolved in 250 ml EtOH and hydrogenated in the presence of 1.1 g Pd/C (10%) under atmospheric pressure of $H_2$ at r.t. After 16 hours the reaction was complete and the catalyst was filtered off and the solvent was removed under reduced pressure to give 6.6 g (32 mmol, 100%) (3R,4R)-4-benzyl-3,4-dihydroxy-piperidine as an oil.

MS: m/e=207.1(M), $[\alpha]_D^{20}$=−42.3(c=1.00, ethanol).

EXAMPLE 11

(3S), (4S)-4-Benzyl-3,4-Dihydroxy-Piperidine (3S,4S)-4-benzyl-3,4-dihydroxy-piperidine-1-carboxylic acid benzyl ester 8.2 g (24 mmol) was dissolved in 250 ml EtOH and hydrogenated in the presence of 1.1 g Pd/C, (10%)under atmospheric pressure at r.t. After 16 hours the reaction was complete and the catalyst was filtered off and the solvent was removed under reduced pressure to give 5.5 g (quant., ~95% purity) (3S,4S)-4-Benzyl-3,4-dihydroxy-piperidine as an oil.

MS: m/e=207.1(M), $[\alpha]_D^{20}$=+42.57 (c=1.05, ethanol).

EXAMPLE 12

(3R,4R) and (3S,4S)-4-Benzyl-1-[2-(4-Benzyloxy-Phenoxy)-Ethyl]-Piperidine-3,4-Diol To a solution of 0.2 g (1.0 mmol) (3R,4R) and (3S,4S)-4-benzyl-3,4-dihydroxy-piperidine in 10 ml DMF were added 297 mg (1.0 mmol) 1-benzyloxy-4-(2-chloro-ethoxy)-benzene and 0.2 g (1.5 mmol) $K_2CO_3$ and the reaction mixture was heated to 90° C. for 16 hours. After the addition of water, the aqueous phase was extracted three times with ethyl acetate and the combined organic layers were washed with water, dried over $MgSO_4$ and the solvent was removed under reduced pressure to give 551 mg (100%, ~80% purity) (3R,4R) and (3S,4S)-4-benzyl-1-[2-(4-benzyloxy-phenoxy)-ethyl]-piperidine-3,4-diol as a solid.

MS: m/e=434.5(M+1).

EXAMPLE 13

(3R,4R)-4-Benzyl-1-[2-(4-Benzyloxy-Phenoxy)-Ethyl]-Piperidine-3,4-Diol

To a solution of 5.0 g (24 mmol) (3R,4R)-4-benzyl-3,4-dihydroxy-piperidine in 150 ml DMF were added 7.4 g (24 mmol) 1-benzyloxy-4-(2-chloro-ethoxy)-benzene and 5.0 g (36 mmol) $K_2CO_3$ and the reaction mixture was heated to 90° C. for 72 hours. After the addition of water the aqueous phase was extracted three times with ethyl acetate and the combined organic layers were washed with water, dried over $MgSO_4$ and the solvent was removed under reduced pressure to give 10.5 g (24 mmol, 100%) (3R,4R)-4-benzyl-1-[2-(4-benzyloxy-phenoxy)-ethyl]-piperidine-3,4-diol as a solid.

MS: m/e=434.5(M+1), $[\alpha]_D^{20}$=−27.5 (c=0.95, $CH_2Cl_2$).

EXAMPLE 14

(3S,4S)-4-Benzyl-1-[2-(4-Benzyloxy-Phenoxy)-Ethyl]-Piperidine-3,4-Diol

To a solution of 5.0 g (24 mmol) (3S,4S)-4-benzyl-3,4-dihydroxy-piperidine in 150 ml DMF were added 7.4 g (24 mmol) 1-benzyloxy-4-(2-chloro-ethoxy)-benzene and 5.0 g (36 mmol) $K_2CO_3$ and the reaction mixture was heated to 90° C. for 72 hours. After the addition of water the aqueous phase was extracted three times with ethyl acetate and the combined organic layers were washed with water, dried over $MgSO_4$ and the solvent was removed under reduced pressure to give 10.9 g (quant., ~95% purity) (3S,4S)-4-benzyl-1-[2-(4-benzyloxy-phenoxy)-ethyl]-piperidine-3,4-diol as a solid.

MS: m/e=434.5(M+1), $[\alpha]_D^{20}$=+26.2(c=1.04, $CH_2Cl_2$).

EXAMPLE 15

(3R,4R) and (3S,4S)-4-Benzyl-1-[2-(4-Hydroxy-Phenoxy)-Ethyl]-Piperidine-3,4-Diol (3R,4R) and (3 S,4S)-4-benzyl-1-[2-(4-benzyloxy-phenoxy)-ethyl]-piperidine-3,4-diol 550 mg (1.3 mmol) was dissolved in 10 ml EtOH and hydrogenated in the presence of 100 mg Pd/C (10%) under atmospheric pressure at 50° C. After 4 hours the reaction was complete and the catalyst was filtered off and the solvent was removed under reduced pressure to give the crude product. Purification by chromatography (CH$_2$Cl$_2$/MeOH 9:1) yielded 249 mg (0.73 mmol, 56%) (3R,4R) and (3S,4S)-4-benzyl-1-[2-(4-hydroxy-phenoxy)-ethyl]-piperidine-3,4-diol as a solid.

MS: m/e=344.4(M+1).

EXAMPLE 16

(3R,4R)-4-Benzyl-1-[2-(4-Hydroxy-Phenoxy)-Ethyl]-Piperidine-3,4-Diol (3R,4R)-4-benzyl-1-[2-(4-benzyloxy-phenoxy)-ethyl]-piperidine-3,4-diol 10.3 g (24 mmol) was dissolved in 300 ml EtOH and hydrogenated in the presence of 1.1 g Pd/C (10%) under atmospheric pressure at 50° C. After 4 hours the reaction was complete and the catalyst was filtered off and the solvent was removed under reduced pressure to give the crude product. Purification by chromatography (CH$_2$Cl$_2$/MeOH 10:1) and crystallization from ethyl acetate and hexane yielded then 4.6 g (10.6 mmol, 45%) (3R,4R)-4-benzyl-1-[2-(4-hydroxy-phenoxy)-ethyl]-piperidine-3,4-diol as a solid.

MS: m/e=344.4(M+1), $[\alpha]_D^{20}$=−36.2(c=1.03, CH$_2$Cl$_2$).

EXAMPLE 17

(3S,4S)-4-Benzyl-1-[2-(4-Hydroxy-Phenoxy)-Ethyl]-Piperidine-3,4-Diol (3S,4S)-4-Benzyl-1-[2-(4-benzyloxy-phenoxy)-ethyl]-piperidine-3,4-diol 10.3 g (24 mmol) was dissolved in 300 ml EtOH and hydrogenated in the presence of 1.1 g Pd/C (10%) under atmospheric pressure at 50° C. After 4 hours the reaction was complete and the catalyst was filtered off and the solvent was removed under reduced pressure to give the crude product. Purification by chromatography (CH$_2$Cl$_2$/MeOH 10:1) and crystallization from ethyl acetate and hexane yielded then 5.7 g (16.6 mmol, 69%) (3S,4S)-4-benzyl-1-[2-(4-hydroxy-phenoxy)-ethyl]-piperidine-3,4-diol as a solid.

MS: m/e=344.3(M+1), $[\alpha]_D^{20}$=+37.1(c=1.04, CH$_2$Cl$_2$).

| Tablet Formulation (Wet Granulation) | | | | |
|---|---|---|---|---|
| Ingredients | mg/tablet | | | |
| 1. Active compound | 5 | 25 | 100 | 500 |
| 2. Lactose Anhydrous DTG | 125 | 105 | 30 | 150 |
| 3. Sta-Rx 1500 | 6 | 6 | 6 | 30 |
| 4. Microcrystalline Cellulose | 30 | 30 | 30 | 150 |
| 5. Magnesium Stearate | 1 | 1 | 1 | 1 |
| TOTAL | 167 | 167 | 167 | 831 |

Manufacturing Procedure:
1. Mix Items 1, 2, 3 and 4 and granulate with purified water.
2. Dry the granulation at 50° C.
3. Pass the granulation through suitable milling equipment.
4. Add Item 5 and mix for three minutes; compress on a suitable press.

| Capsule Formulation | | | | |
|---|---|---|---|---|
| Ingredients | mg/capsule | | | |
| 1. Active compound | 5 | 25 | 100 | 500 |
| 2. Hydrous Lactose | 159 | 123 | 148 | — |
| 3. Corn Starch | 25 | 35 | 40 | 70 |
| 4. Talc | 10 | 15 | 10 | 25 |
| 5. Magnesium Stearate | 1 | 2 | 2 | 5 |
| TOTAL | 200 | 200 | 300 | 600 |

Manufacturing Procedure;
1. Mix Items 1, 2, and 3 in a suitable mixer for 30 minutes.
2. Add Items 4 and 5 and mix for 3 minutes.
3. Fill into a suitable capsule.

What is claimed is:

1. A compound with the structure of formula I

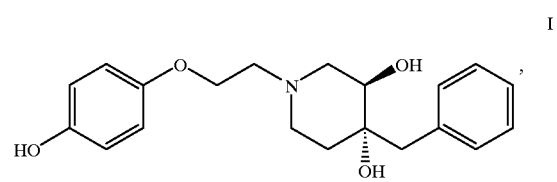

its R,R- and S,S-enantiomers and their pharmaceutically acceptable acid addition salts.

2. A compound of formula I in accordance with claim 1, selected from the group consisting of (3R, 4R) 4-benzyl-1-[2-(4-hydroxy-phenoxy)-ethyl]-piperidine-3,4-diol, (3S, 4S) 4-benzyl-1-[2-(4-hydroxy-phenoxy)-ethyl]-piperidine-3,4-diol and racemic mixtures thereof.

3. A compound of formula I in accordance with claim 2, which is (3 R,4R)-4-benzyl-1-[2-(4-hydroxy-phenoxy)-ethyl]-piperidine-3,4-diol.

4. A compound of formula I in accordance with claim 2, which is (3S,4S)-4-benzyl-1-[2-(4-hydroxy-phenoxy)-ethyl]-piperidine-3,4-diol.

5. A medicament containing one or more compounds according to claim 2 and pharmaceutically inert excipients.

6. A medicament in accordance with claim 5 useful for the treatment of diseases including disease states caused by overactivation of respective NMDA receptor subtypes including acute forms of neurodegeneration caused by stroke or brain trauma; chronic forms of neurodegeneration such as Alzheimer's disease, Parkinson's disease, Huntington's disease or ALS (amyotrophic lateral sclerosis); neurodegeneration associated with bacterial or viral infections, and, diseases such as schizophrenia, anxiety, depression and chronic/acute pain.

7. A process for preparing a compound of formula I as defined in claim 1, which process comprises reacting a compound of formula

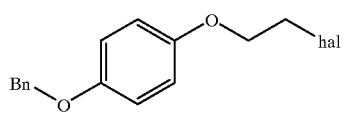

with a compound of formula

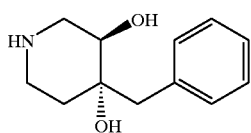

(rac)

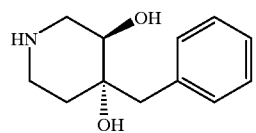

(R,R)

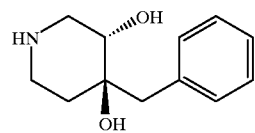

(S,S)

and deprotecting the hydroxy group to give compounds of formulae

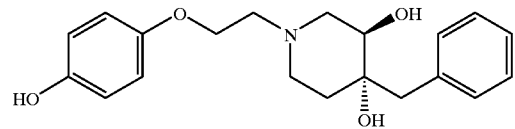

(rac)

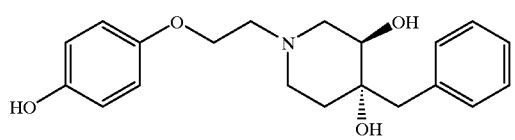

(R,R)

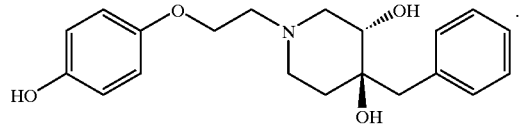

(S,S)

8. The method of claim 7 further comprising reacting the compounds obtained with pharmaceutically acceptable inorganic and organic acids thereby forming addition salts.

9. The method of claim 8 wherein said pharmaceutically acceptable acids are selected from the group consisting of hydrochloric acid, nitric acid, sulfuric acid, lactic acid, phosphoric acid, citric acid, formic acid, fumaric acid, maleic acid, acetic acid, succinic acid, tartaric acid, methane-sulfonic acid, and p-toluenesulfonic acid.

10. A method of treatment of a disease state caused by malfunction of the NMDA receptor subtypes comprising administering to a patient in need of such treatment, an effective amount of a composition for treating said disease state, said composition containing an effective amount of a compound that functions as a NDMA receptor subtype specific blocker in a pharmaceutically acceptable carrier, said compound having the structure of formula I 11. The method of treatment of claim 10 wherein the disease state being treated consists of acute forms of neurodegeneration caused by stroke or brain trauma; chronic forms of neurodegeneration such as Alzheimer's disease, Parkinson's disease, Huntington's disease or ALS (amyotrophic lateral sclerosis); neurodegeneration associated with bacterial or viral infections, and, diseases such as schizophrenia, anxiety, depression and chronic/acute pain.

* * * * *

UNITED STATES PATENT AND TRADEMARK OFFICE
CERTIFICATE OF CORRECTION

PATENT NO.   : 6,432,985 B2
DATED        : August 13, 2002
INVENTOR(S)  : Alexander Alanine et al.

It is certified that error appears in the above-identified patent and that said Letters Patent is hereby corrected as shown below:

Column 3,
Line 38, delete "VII" and insert -- VIII --

Column 17,
Line 3, delete "VII" and insert -- VIII --.

Signed and Sealed this

Fourth Day of February, 2003

JAMES E. ROGAN
*Director of the United States Patent and Trademark Office*